United States Patent [19]

Schoch et al.

[11] Patent Number: 5,202,038
[45] Date of Patent: Apr. 13, 1993

[54] SALTS OF FATTY AMINES AND OF POLYFLUORO-CARBOXYLIC ACIDS AND THEIR USE AS ADDITIVES FOR LUBRICANTS

[75] Inventors: Elisabeth Schoch, Rambouillet; Christian Collette, Paris, both of France

[73] Assignee: ELF Atochem S.A., Puteaux, France

[21] Appl. No.: 842,679

[22] Filed: Feb. 27, 1992

[30] Foreign Application Priority Data

Feb. 27, 1991 [FR] France ................................ 91 02345

[51] Int. Cl.$^5$ .......................................... C10M 131/12
[52] U.S. Cl. .................................... 252/33.6; 252/34; 252/51
[58] Field of Search ........................... 252/34, 51, 33.6

[56] References Cited

U.S. PATENT DOCUMENTS

| | | | |
|---|---|---|---|
| 2,951,051 | 8/1960 | Tiers | 260/23 |
| 3,565,926 | 2/1971 | Furey | 260/404 |
| 3,634,242 | 1/1972 | Bosniack et al. | 252/33.6 |
| 3,784,471 | 1/1974 | Kaiser | 252/54.6 |
| 4,107,055 | 8/1978 | Sukornick et al. | 252/8.6 |
| 4,832,859 | 5/1989 | Basset et al. | 252/51 |
| 4,853,141 | 8/1989 | Durual et al. | 252/51 |
| 4,859,357 | 8/1989 | Germanaud et al. | 252/58 |
| 5,039,438 | 8/1991 | Thermet et al. | 252/51 |
| 5,091,269 | 2/1992 | Kondo et al. | 252/51.5 A |

FOREIGN PATENT DOCUMENTS

| | | |
|---|---|---|
| 2026493 | 9/1970 | France . |
| 2520377 | 7/1983 | France . |
| 2599378 | 12/1987 | France . |
| 2616781 | 12/1988 | France . |
| 2616783 | 12/1988 | France . |

OTHER PUBLICATIONS

Long Chain Alkanoic and Alkenoic Acids with Perfluoroalkyl Terminal Segments, Journal of Organic Chemistry, vol. 27, Dec. 1962, pp. 4491–4498.
European Search Report dated Nov. 14, 1991.

*Primary Examiner*—Jacqueline Howard
*Attorney, Agent, or Firm*—Morgan & Finnegan

[57] ABSTRACT

The invention relates to the salts formed by a fatty amine with a mixture containing at least one monocarboxylic acid $R_F(CH_2)_{10}COOH$ and at least one dicarboxylic acid of formula:

$$R_FCH_2CH(CH_2)_8COOH$$
$$|$$
$$R_FCH_2CH(CH_2)_8COOH$$

where $R_F$ denotes a $C_4$–$C_{16}$ perfluoroalkyl radical, wherein these salts can be employed as antiwear additives for lubricants.

12 Claims, No Drawings

SALTS OF FATTY AMINES AND OF POLYFLUORO-CARBOXYLIC ACIDS AND THEIR USE AS ADDITIVES FOR LUBRICANTS

The present invention relates to the field of fluorinated products and that of lubricants. It relates more particularly to new salts of polyfluorocarboxylic acids which can be employed as antiwear additives for lubricants.

BACKGROUND OF THE INVENTION

The use of certain organofluorine derivatives as additives for lubricating compositions is known; for example the use of salts of aliphatic amines and of perhalogenated monocarboxylic acids such as the acid $Cl(CF_2CFCl)_3CF_2COOH$ and the acid $C_7F_{15}COOH$ has been described in U.S. Pat. No. 3,565,926, just as the use of the derivatives obtained by reacting an aromatic amine and a perfluorinated monocarboxylic acid (for example $C_7F_{15}COOH$) has been disclosed in Patent FR 2,026,493. However, these carboxylic derivatives have the disadvantage of losing their antiwear effectiveness in the presence of conventional additives such as dispersant-detergent additives, either as a result of physico-chemical interactions which prevent their absorption at the surfaces to be lubricated, or because of chemical interactions, in particular when the dispersant-detergent additives are neutral or overbased salts of alkaline-earth metals.

The use of amines or of aminoalcohols containing a polyfluorinated chain (Patent FR 2,520,377) and that of derivatives of these aminoalcohols (Patents FR 2,599,378, 2,616,781 and 2,616,783) as antiwear additives for lubricants has also been proposed.

There are also known certain polyfluorocarboxylic acids of formulae:

(I)

(II)

in which $R_F$ denotes a perfluoroalkyl radical.

The use of these acids or of their derivatives as additives for lubricants does not appear to have yet been envisaged. According to U.S. Pat. No. 2,951,051, which describes 11-(perfluorooctyl)undecanoic acid, its sodium and potassium salts and its chromium complex (Examples II and V), the monocarboxylic acids (I) are prepared from 10-undecenoic acid and a perfluoroalkyl sulphochloride or iodide. U.S. Pat. No. 4,107,055, relating to the use of diacids and of their alkali metal salts as fluorinated surface-active agents in antisoiling compositions based on unhalogenated polymer latexes for textiles, indicates that the diacids (II) can be prepared by the action of zinc on the iodoacids $R_FCH_2CHI(CH_2)_mCOOH$ in ethanol.

SUMMARY OF THE INVENTION

It has now been found that the salts formed form a fatty amine and a mixture of the polyfluorinated acids (I) and (II) exhibit a remarkable antiwear effectiveness, much higher than that of the salts of the perhalogenated monocarboxylic acids and at least equal to, or even higher than, that of the additives of the amine or aminoalcohol type.

An object of the invention is the salts formed from a fatty amine and a mixture containing at least one monocarboxylic acid of formula (I) and at least one dicarboxylic acid of formula (II), it being possible for the perfluoroalkyl radical $R_F$ to be linear or branched and to contain from 4 to 16 carbon atoms, preferably 6 to 12.

Another object of the invention is the use of these salts as antiwear additives for lubricants.

DETAILED DESCRIPTION OF THE INVENTION

The mixture of acids (I) and (II) is advantageously obtained by reacting a perfluoroalkyl iodide $R_FI$ with 10-undecenoic acid in the presence of zinc and in a dichloromethane medium at a temperature of approximately 50° C. After removal of zinc in the form of chloride, the mixture of mono- and dicarboxylic acids is extracted with ether. When substantially equimolar quantities of $R_FI$, 10-undecenoic acid and zinc are employed, a mixture is generally obtained in which the content of monoacid (I) varies between approximately 60 and 75 mol %, this content being proportionately higher with a smaller the number of carbon atoms in the starting $R_FI$ material. If desired, the reaction may be directed towards the predominant formation of dicarboxylic acid (II) by using a smaller quantity of zinc, for example 0.5 mol of zinc per mole of $R_FI$.

For economical and practical reasons it may be found advantageous to start with an industrial mixture of perfluoroalkyl iodides, which results in a complex mixture of a number of monoacids and diacids which have different radicals $R_F$.

The fatty amine to be employed to form the salts according to the invention may be chosen from primary, secondary or tertiary aliphatic or cycloaliphatic amines containing from 12 to 24 carbon atoms in all, preferably from 16 to 20 carbon atoms. As nonlimiting examples of such amines there may be mentioned more particularly N,N-bis(2-ethylhexyl)amine, dioctylamine, oleylamine and octadecylamine. Naturally, it would not constitute a departure from the scope of the present invention to use a mixture of fatty amines.

The salts according to the invention can be prepared in a manner known per se, by employing a quantity of fatty amine(s) which is sufficient to neutralise the acidic functional groups.

The quantity of salts according to the invention to be added to a lubricating oil to obtain an antiwear effectiveness is at least 0.01 % relative to the weight of the oil and is preferably between 0.05 and 0.5%.

The lubricating oil may be a mineral oil, a synthetic hydrocarbon or a synthetic oil belonging to the following different classes: glycols, glycol ethers, glycol esters, polyoxyalkylene glycols, their ethers and their esters, and esters of monocarboxylic or polycarboxylic acids and of monoalcohols or polyalcohols, this list not being limiting.

When the lubricant bases employed are petroleum cuts intended for the manufacture of engine oils, such as the "Neutral Solvent" bases, the salts according to the invention are advantageously used in combination with conventional dispersant-detergent additives such as calcium or barium alkylarylsulphonates and alkylphenates, or "ashless" dispersants such as succinic derivatives. The dispersant-detergent additives promote the solubilization of the fluorinated additives in the oil without affecting the antiwear properties of the latter and without losing their own power.

The addition of salts according to the invention to formulated oils already containing additives such as zinc alkyldithiophosphates brings about an appreciable improvement in the antiwear power and an increase in the load capacity of these oils without disturbing the properties contributed by the other additives: for example dispersiveness, detergency and anticorrosion power.

The replacement, in the oil formulations for internal combustion engines, of all or part of the zinc dithiophosphate employed as antiwear additive by 0.1 to 0.2% of salts according to the invention makes it possible to reach a level of protection against wear which is equal to o higher than that obtained with this conventional additive.

The salts according to the invention can therefore be employed either as a replacement for zinc alkyldithiophosphates in lubricating oils for petrol engines or diesel engines, or as an extra additive in these oils.

The example and the tests which follow illustrate the invention without limiting it. The percentages shown are expressed on a weight basis, unless stated otherwise.

EXAMPLE a) Preparation of the Mixtures of Polyfluorocarboxylic Acids 43.7 g of zinc are dispersed in a solution of 123.8 g of 10-undecenoic acid in 200 ml of methylene chloride in a 1-litre conical flask, and 300 g of perfluorohexyl iodide are then added dropwise with stirring. The reaction mixture is heated to about 50° C. at the beginning of the addition until a reflux appears. After the end of the addition (duration: 2 hours) stirring is continued for 15 hours.

300 ml of an aqueous solution containing 20% of hydrochloric acid are added to the pasty mixture thus obtained to destroy the zinc salts, and the organic phase is then extracted with ether. The ether phase is then washed two or three times with distilled water and then decolorised by treatment with the aid of a solution containing 10% of sodium thiosulphate.

After removal of the ether under reduced pressure a product (A6) is obtained, which melts at approximately 50° C. and which contains 65 mol % of 11-(perfluorohexyl)undecanoic acid: $C_6F_{13}(CH_2)_{10}COOH$ and 35 mol % of 10,11-bis[(perfluorohexyl)methyl]-eicosanedioic acid:

This molar distribution was determined by integrating the signals obtained in $^{19}F$ NMR analysis.

The acidity of the product, which is 2.04 acidic functional groups per kilogram, was determined by potentiometric titration with alcoholic potassium hydroxide.

Other mixtures of polyfluorocarboxylic acids (I) and (II) were obtained by proceeding in the same manner starting with $C_4F_9I$, $C_8F_{17}I$ and with an industrial cut of different iodides $C_nF_{2n+1}I$ which has the following composition:

| n | mol % |
|---|---|
| 6 | 52.9 |
| 7 | 0.9 |
| 8 | 31.3 |
| 9 | 0.3 |
| 10 | 8.9 |
| 12 | 2.9 |
| 14 | 0.8 |
| 16 | 0.4 | and an average molecular mass of 578.4. Table I below shows the quantities of reactants employed for these tests and the molar distribution of the mono- and dicarboxylic acids in the products obtained.

TABLE I

| $R_F$: | $C_4F_9$ | $C_8F_{17}$ | $C_nF_{2n+1}$ cut |
|---|---|---|---|
| Quantities employed: | | | |
| $R_FI$ (g) | 300 | 300 | 300 |
| zinc (g) | 56.3 | 35.7 | 33.7 |
| 10-undecenoic acid (g) | 159.5 | 101.1 | 95.4 |
| $CH_2Cl_2$ solvent (ml) | 200 | 150 | 150 |
| Product obtained: | $A_4$ | $A_8$ | $A_n$ |
| Monoacid (I) | 72% | 64% | 59% |
| Diacid (II) | 28% | 36% | 41% |
| Melting range (°C.) | approx. 50 | 50–60 | 50–60 |
| Acidic functional groups/kg | 2.51 | 1.82 | 1.83 | b) Preparation of the N,N-bis(2-ethylhexyl)-Amine Salts 120 g of the mixture of acids obtained above (product $A_6$) are melted at 60°–70° C. in a conical flask. After complete melting 60 g of N,N-bis(2-ethylhexyl)amine are added with stirring and stirring is then continued for 15 minutes to homogenize the mixture. The latter is then left to cool to room temperature.

This gives 180 g of salt (denoted S6 below) of the polyfluorocarboxylic acids (I) and (II) with $R_F=C_6F_{13}$.

By proceeding in a similar manner with the products $A_4$, $A_8$ and $A_n$ of the preceding table the corresponding salts are obtained, which are identified below by the abbreviations $S_4$, $S_8$ and $S_n$ respectively.

ANTIWEAR TESTS

The antiwear power of lubricating compositions containing the mineral oil 200 Neutral Solvent as base oil and a salt according to the invention as additive was determined with the aid of a Shell 4-ball EP machine the description of which appears in the "Annual Book of ASTM Standards", Part 24 (1979), pages 680–688.

The test consists in rotating a ball 12 mm in diameter at a speed of rotation of 1500 rev/min on three other balls kept stationary and covered with lubricant being studied. A load of 40 daN is applied by a lever system which pushes the three stationary balls towards the upper ball placed in a mandrel.

The antiwear effectiveness of a lubricant is determined by the mean value of the diameters of the wear imprints on the three stationary balls after one hour's operation.

Table II below collates the results obtained with different salts according to the invention, employed in a proportion of 0.1% based on the weight of oil.

TABLE II

| Fluoro additive | Wear diameter in mm | | |
|---|---|---|---|
| | 30° C. | 80° C. | 120° C. |
| None | 0.90 | 0.80 | 1.39 |

TABLE II-continued

| Fluoro additive | Wear diameter in mm | | |
|---|---|---|---|
| | 30° C. | 80° C. | 120° C. |
| $S_4$ | 0.39 | 0.41 | 0.67 |
| $S_6$ | 0.39 | 0.40 | 0.39 |
| $S_8$ | 0.38 | 0.38 | 0.41 |
| $S_n$ | 0.42 | 0.42 | 0.42 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Fatty amine salts of a mixture containing at least one monocarboxylic acid of formula:

$$R_F(CH_2)_{10}COOH \qquad (I)$$

and at least one dicarboxylic acid of formula:

$$R_FCH_2CH(CH_2)_8COOH \\ | \\ R_FCH_2CH(CH_2)_8COOH \qquad (II)$$

where $R_F$ denotes a linear or branched perfluoroalkyl radical containing from 4 to 16 carbon atoms and wherein the molar proportion of monocarboxylic acid salt (I) is between about 59% and 75%.

2. Salts according to claim 1, in which the radicals $R_F$ contain from 6 to 12 carbon atoms.

3. Salts according to claim 1, in which the fatty amine is chosen from aliphatic or cycloaliphatic amines containing from 12 to 24 carbon atoms or a mixture thereof.

4. Salts according to claim 1, in which the fatty amine is N,N-bis(2-ethylhexyl)amine.

5. Lubricants containing at least one fatty amine salt according to claim 1 as a additive.

6. Lubricants according to claim 5, in which the fatty amine salt content is at least 0.01% by weight.

7. Lubricants according to claim 5, in which the fatty amine salts are used in combination with conventional additives.

8. The lubricants of claim 6, wherein the fatty amine salt content is between 0.01% and 0.5% by weight.

9. The lubricants of claim 6, wherein the fatty amine salt content is between 0.05% and 0.05%.

10. A process of reducing wear by using a lubricant including the fatty amine salt of claim 1.

11. The salts according to claim 3, wherein the aliphatic or cycloaliphatic amines contain from 16 to 20 carbon atoms.

12. A process for preparing the fatty amine salts of claim 1 comprising heating a mixture of polyfluorocarboxylic acid containing at least one dicarboxylic acid of formula $R_F(CH_2)_{10}COOH$ with at least one dicarboxylic acid of formula II $$R_FCH_2CH(CH_2)_8COOH \\ | \\ R_FCH_2CH(CH_2)_8COOH$$

where $R_F$ denotes a linear or branched perfluoroalkyl radical containing from 4 to 16 carbon atoms, until the mixture is melted, adding and mixing the mixture with a fatty amine to form a fatty amine salt.

* * * * *

UNITED STATES PATENT AND TRADEMARK OFFICE
CERTIFICATE OF CORRECTION

PATENT NO. : 5,202,038

DATED : April 13, 1993

INVENTOR(S) : SCHOCH, et al.

It is certified that error appears in the above-identified patent and that said Letters Patent is hereby corrected as shown below:

Col. 6, claim 9, line 2, delete "between 0.05% and 0.05%" and insert --between 0.05 and 0.5%--.

Signed and Sealed this

Eighteenth Day of January, 1994

Attest:

BRUCE LEHMAN

*Attesting Officer*     *Commissioner of Patents and Trademarks*